US005665566A

United States Patent [19]
LaVallie

[11] Patent Number: 5,665,566
[45] Date of Patent: Sep. 9, 1997

[54] CLONING OF ENTEROKINASE AND METHOD OF USE

[75] Inventor: Edward R. LaVallie, Tewksbury, Mass.

[73] Assignee: Genetics Institute, Inc., Cambridge, Mass.

[21] Appl. No.: 200,900

[22] Filed: Feb. 23, 1994

Related U.S. Application Data

[63] Continuation of Ser. No. 5,944, Jan. 15, 1993, abandoned.

[51] Int. Cl.$^6$ .......................... C12N 15/63; C12N 15/70; C12N 15/79; C12N 15/57
[52] U.S. Cl. ........................................................ 435/69.3
[58] Field of Search .................. 424/94.63; 536/27, 536/23.2, 27.2; 435/69.1, 69.3, 252.3, 320.1

[56] References Cited

U.S. PATENT DOCUMENTS

| | | | |
|---|---|---|---|
| 4,745,069 | 5/1988 | Mayne et al. ........................... | 435/68 |
| 4,769,326 | 9/1988 | Rutter .................................... | 435/68 |
| 4,828,988 | 5/1989 | Bollen et al. .......................... | 435/68 |
| 4,870,008 | 9/1989 | Brake .................................... | 435/70 |
| 5,270,181 | 12/1993 | McCoy et al. ......................... | 435/69.7 |
| 5,292,646 | 3/1994 | McCoy et al. ......................... | 435/69.7 |

FOREIGN PATENT DOCUMENTS

| | | |
|---|---|---|
| 0259953 | 6/1987 | European Pat. Off. . |
| 0237966 | 9/1987 | European Pat. Off. . |
| WO88/00598 | 1/1988 | WIPO . |

OTHER PUBLICATIONS

Burgess et al. J. Cell Biology 111:2129-2137 Nov. 1990.
Lazar et al. Mol. Cell Biology 8(3):1247-1252 1988 Mar. 1988.
Bowie et al. Science 247:1306-1310 Mar. 16, 1990.
Pramego Protocols and Applications Guide, Mar. 1991 pp. 156, 166-168.
Young and Davis 80: 1194-98 1983.
Miyoshi et al. Gastroenterol. Jpn 25(3) 320-27 (see abstract) 1990.
Miyoshi et al. Igaku No Ayumi 149(13) 951-2 (see abstract) 1989.
Naigai et al., Methods Enzymol. 153:461-481(1987).
Hammond et al., BioPharm 16-23 (1991).
Yansura, Methods Enzymol. 165:161-166 (1990).
Nilsson et al., EMBO J. 4:1075-1080 (1985).
Smith et al., Gene 67:31-40 (1988).
Maina et al.:Gene 74:365-373 (1988).
Stader et al., Methods in Enzymol. 165:166-187 (1990).
LaVallie et al., Bio/Technology, in press (1992).
Hopp et al., Bio/Technology 6:1204-1210 (1988).
Light et al., J. Prot. Chem. 10:475-480 (1991).

Saiki et al., Science 230:1350-1354 (1985).
Mullis et al., Cold Spring Harbor Symposia On Quantitative Biology, vol. LI:263-273 (1986).
Mullis et al., Methods Enzymol. 155:335-(1987).
Sambrook et al, Molecular Cloning, a Laboratory Manual, second edition, Cold Spring Harbor Laboratory Press (1989)—(* readily available reference book; copy not supplied.).
Norrander et al., Gene 26:101-106 (1983).
Liepnieks et al., J. Biol. Chem. 254:1677-1683 (1979).
Leytus et al., Biochemistry 27:1067-1074 (1988).
Chirgwin et al., Biochemistry 18:5294- (1979).
Padgett et al., Ann. Rev. Biochem. 55:1119-1150 (1986).
Saiki et al., Science 239:487- (1988).
Van den Ouweland et al., Nucleic Acids Res. 18:664 (1990).
Wise et al., PNAS 87:9378-9382 (1990).
Light et al., J. Biol. Chem. 259:13195-13198 (1984).
Obaru et al., J. Biochem. 99:885-894 (1986).
Weiser et al., PNAS 86:7522-7526 (1989).
Le Heuron et al., Eur. J. Biochem. 193:767-773 (1990).
Shimatake et al., Nature 292:128-132 (1981).
Olins et al., J. Biol. Chem. 264:16973-16976 (1989).
Blow, Acc. Chem. Res. 9:145-152 (1976).
Maroux et al., J. Biol. Chem. 246:5031-5039 (1971).
Grant et al., Biochem. J. 155:243-254 (1976).
Baratti et al., Biochem. Biophys. Acta 321:632-638 (1973).
Baratti et al., Biochem. Biophys. Acta 452:452-496 (1976).
Hadorn et al., Lancet 1:812-813 (1969).
Tarlow et al., Arch. Dis. Child. 45:651-655 (1970).
Lebenthal et al., Gastroenterology 70:508-512 (1976).
Cool et al., J. Biol. Chem. 262:13662-13673 (1987).
Anderson et al., Biochemistry 16:3354-3360 (1977).
Hatsuzawa et al., J. of Biol. Chem. 267:16094-16099 (1992).
Brenner et al., PNAS 89:922-926 (1992).
Light et al., Anal. Biochem. 106:199(1980).
Grant et al., Biochem. Biophys. Acta. 567:207(1979).
Miller et al., Genetic Engineering 8:277-98 (Plenum Press 1986).
Gospodarowicz et al., J. Cell. Phys. 122:323:32 (1985).
Iwane et al., Biochem. and Biophys. Res. Comm. 146:470-77 (1987).
Fox et al., J. Biol. Chem. 263:18452-58 (1988).
Norrander et al., Gene 26:101-106(1983) HincII-HindIII vector.
Rehemtulla et al., *Blood* 79:2349(1992).
Julius et al., *Cell* 32:839(1983).
Julius et al., *Cell* 37:1075 (1984).

*Primary Examiner*—Anthony C. Caputa
*Attorney, Agent, or Firm*—M. C. Meinert

[57] ABSTRACT

Provided are nucleic acid sequence sequences encoding enterokinase activity, the expression products thereof, and methods for using same.

20 Claims, 4 Drawing Sheets

FIGURE 1

```
   1  CGGAGCTTGTGATGGAAGATTTTTGTTGACTGGATCTTCTGGGTCCTTTG    50
  51  AGGCTCTGCATTATCCCAAGCCTTCTAATAATACAAGCGCTGTTTGTCGG   100
 101  TGGATTATACGTGTAAACCAAGGACTTTCCATTCAACTGAACTTCGATTA   150
 151  TTTTAATACATATTATGCAGATGTATTAAATATTTATGAAGGAATGGGTT   200
 201  CAAGCAAGATTTTAAGAGCTTCTCTCTGGTCAAATAATCCTGGCATAATT   250
 251  AGGATTTTTTCCAATCAAGTTACTGCCACTTTTCTTATACAGTCTGATGA   300
 301  AAGTGATTATATTGGCTTCAAAGTAACATACACTGCATTTAACAGCAAAG   350
 351  AGCTTAATAATTATGAGAAAATCAACTGTAATTTTGAAGATGGCTTCTGT   400
 401  TTCTGGATCCAGGATCTAAATGATGACAATGAGTGGGAAAGGACTCAGGG   450
 451  AAGCACCTTTCCTCCATCTACTGGACCAACTTTTGACCACACTTTTGGCA   500
 501  ATGAGTCAGGATTTTACATTTCCACCCCAACTGGACCAGGAGGAAGACGA   550
 551  GAAAGAGTAGGACTTTTAACTCTCCCTTTAGATCCCACTCCTGAACAAGC   600
 601  CTGCCTTAGTTTCTGGTATTATATGTATGGTGAAAATGTTTACAAACTAA   650
 651  GCATTAATATCAGCAGTGACCAAAACATGGAGAAGACAATTTTCCAAAAA   700
 701  GAAGGAAATTATGGACAAAATTGGAACTATGGACAAGTAACATTAAATGA   750
 751  AACAGTGGAATTTAAGGTTTCTTTCTATGGGTTTAAAAACCAGATCCTGA   800
 801  GTGATATAGCATTGGATGACATTAGCCTAACATATGGGATTTGTAATATG   850
 851  AGTGTCTATCCAGAACCAACTTTAGTCCCAACTCCTCCACCAGAACTTCC   900
 901  CACGGACTGTGGAGGGCCTCATGACCTGTGGGAGCCAAATACAACATTCA   950
 951  CGTCTATAAACTTCCCAAACAGCTACCCTAATCAGGCTTTCTGTATTTGG  1000
1001  AATTTAAATGCACAAAAGGGAAAAAATATTCAGCTCCACTTTCAAGAATT  1050
1051  TGACCTGGAAAATATTGCAGATGTAGTTGAAATCAGAGATGGTGAAGGAG  1100
```

FIGURE 1A

```
1101  ATGATTCCTTGTTCTTAGCTGTGTACACAGGCCCTGGTCCAGTAAACGAT  1150
1151  GTGTTCTCAACCACCAACCGAATGACTGTGCTTTTATCACTGATAATAT   1200
1201  GCTGGCAAAACAGGGATTTAAAGCAAATTTCACTACTGGCTATGGCTTGG   1250
1251  GGATTCCAGAACCCTGCAAGGAAGACAATTTTCAGTGCAAGGATGGGGAG   1300
1301  TGTATTCCGCTGGTGAATCTCTGTGACGGTTTTCCACACTGTAAGGATGG   1350
1351  CTCAGATGAAGCACACTGTGTGCGTCTTCAATGGCACGACAGACAGCA    1400
1401  GTGGTTTGGTGCAGTTCAGGATCCAAAGCATATGGCATGTAGCCTGTGCC   1450
1451  GAGAACTGGACAACCCAGATCTCAGATGATGTGTGTCAGCTGCTGGGACT   1500
1501  AGGGACTGGAAACTCATCCGTGCCAACCTTTTCTACTGGAGGTGGACCAT   1550
1551  ATGTAAATTTAAACACAGCACCTAATGGCAGCTTAATACTAACGCCAAGC   1600
1601  CAACAGTGCTTAGAGGATTCACTGATTTTGCTACAATGTAACTACAAATC   1650
1651  ATGTGGGAAAAAACTGGTGACTCAAGAAGTTAGCCCGAAGATTGTCGGAG   1700
1701  GAAGTGACTCCAGAGAAGGAGCCTGGCCTTGGGTCGTTGCTCTGTATTTC   1750
1751  GACGATCAACAGGTCTGCGGAGCTTCTCTGGTGAGCAGGGATTGGCTGGT   1800
1801  GTCGGCCGCCCACTGCGTGTACGGGAGAAATATGGAGCCGTCTAAGTGGA   1850
1851  AAGCAGTGCTAGGCCTGCATATGGCATCAAATCTGACTTCTCCTCAGATA   1900
1901  GAAACTAGGTTGATTGACCAAATTGTCATAAACCCACACTACAATAAACG   1950
1951  GAGAAAGAACAATGACATTGCCATGATGCATCTTGAAATGAAAGTGAACT   2000
2001  ACACAGATTATATACAGCCTATTTGTTACCAGAAGAAAATCAAGTTTTT   2050
2051  CCCCCAGGAAGAATTTGTTCTATTGCTGGCTGGGGGCACTTATATATCA   2100
2101  AGGTTCTACTGCAGACGTACTGCAAGAAGCTGACGTTCCCCTTCTATCAA   2150
2151  ATGAGAAATGTCAACAACAGATGCCAGAATATAACATTACGGAAAATATG   2200
2201  GTGTGTGCAGGCTATGAAGCAGGAGGGTAGATTCTTGTCAGGGGATTC    2250
```

FIGURE 1B

```
2251  AGGCGGACCACTCATGTGCCAAGAAAACAACAGATGGCTCCTGGCTGGCG  2300
2301  TGACGTCATTTGGATATCAATGTGCACTGCCTAATCGCCCAGGGGTGTAT  2350
2351  GCCCGGGTCCCAAGGTTCACAGAGTGGATACAAAGTTTTCTACATTAGAG  2400
2401  TGTTTCCAGAAACAAAGATGAAAATCAGGCAGTTTTCCCATTTCACTTTA  2450
2451  AGAAGCATGGAAATTGAGAGTTAAAAAAATAATAATTTATAAAAGTCTTG  2500
2501  ATTCTTACCTAAGGCACTGAAATGCTACAAAAAAAAAAAAACCGGAATTC  2550
2551  AGCTTGGACTTAACCAGGCTGAACTTGCGGC  2581
```

FIGURE 2

```
            10                      30                     50
             .                       .                      .
GACDGRFLLTGSSGSFEALHYPKPSNNTSAVCRWIIRVNQGLSIQLNFDYFNTYYADVLN
            70                      90                    110
             .                       .                      .
IYEGMGSSKILRASLWSNNPGIIRIFSNQVTATFLIQSDESDYIGFKVTYTAFNSKELNN
           130                     150                    170
             .                       .                      .
YEKINCNFEDGFCFWIQDLNDDNEWERTQGSTFPPSTGPTFDHTFGNESGFYISTPTGPG
           190                     210                    230
             .                       .                      .
GRRERVGLLTLPLDPTPEQACLSFWYYMYGENVYKLSINISSDQNMEKTIFQKEGNYGQN
           250                     270                    290
             .                       .                      .
WNYGQVTLNETVEFKVSFYGFKNQILSDIALDDISLTYGICNMSVYPEPTLVPTPPPELP
           310                     330                    350
             .                       .                      .
TDCGGPHDLWEPNTTFTSINFPNSYPNQAFCIWNLNAQKGKNIQLHFQEFDLENIADVVE
           370                     390                    410
             .                       .                      .
IRDGEGDDSLFLAVYTGPGPVNDVFSTTNRMTVLFITDNMLAKQGFKANFTTGYGLGIPE
           430                     450                    470
             .                       .                      .
PCKEDNFQCKDGECIPLVNLCDGFPHCKDGSDEAHCVRLFNGTTDSSGLVQFRIQSIWHV
           490                     510                    530
             .                       .                      .
ACAENWTTQISDDVCQLLGLGTGNSSVPTFSTGGGPYVNLNTAPNGSLILTPSQQCLEDS
           550                     570                    590
             .                       .                      .
LILLQCNYKSCGKKLVTQEVSPKIVGGSDSREGAWPWVVALYFDDQQVCGASLVSRDWLV
           610                     630                    650
             .                       .                      .
SAAHCVYGRNMEPSKWKAVLGLHMASNLTSPQIETRLIDQIVINPHYNKRRKNNDIAMMH
           670                     690                    710
             .                       .                      .
LEMKVNYTDYIQPICLPEENQVFPPGRICSIAGWGALIYQGSTADVLQEADVPLLSNEKC
           730                     750                    770
             .                       .                      .
QQQMPEYNITENMVCAGYEAGGVDSCQGDSGGPLMCQENNRWLLAGVTSFGYQCALPNRP
           790
GVYARVPRFTEWIQSFLH*
```

CLONING OF ENTEROKINASE AND METHOD OF USE

This is a continuation of application Ser. No. 08/005,944, filed Jan. 15, 1993, now abandoned.

FIELD OF THE INVENTION

The present invention relates generally to the cloning and expression of enterokinase activity and to methods of its making and use.

BACKGROUND OF THE INVENTION

The use of fusion proteins as a tool for recombinant protein production is well known in the biopharmaceutical industry. Fusing the coding sequence for a desired recombinant protein to that of a well-expressed gene has several advantages. Most fusion protein strategies position the protein of interest at the C-terminal end of the highly expressed fusion partner which allows translation initiation to occur on a "proven" gene sequence that is known to be well translated and can help ensure high expression levels. Some fusion partners can coffer many advantageous attributes to the fusion protein, such as specific cellular localization, binding to affinity ligands to aid in purification and detection, and even proteolytic and conformational stability.

While fusion proteins offer numerous advantages, this beneficial physical association of the protein domains can also be problematic when it becomes necessary to separate the two (or more) components from their covalent tethering. The method of protein cleavage must be both specific and efficient and must not yield unwanted side products. This is particularly so when utilizing a fusion protein approach for the production of biopharmaceuticals destined for human use. Ideally, the most useful method allows for cleavage at a specific target sequence without regard for the internal protein sequence and/or without regard for the composition of the fusion partners. The method should produce cleaved product with authentic N- and C-termini, should not modify or otherwise adulterate the desired protein product, and should be tolerant to a wide range of conditions so that reaction components can be tailored to the physical characteristics of the fusion protein without seriously affecting the efficiency of the cleavage reaction. In addition, for biopharmaceutical production and applications, the cleaving reagent should not be from an animal source due to concerns about contamination by infections agents.

An ideal choice for such a "universal" fusion protein cleaving method is use of the mammalian enzyme enterokinase (enteropeptidase). Enterokinase is the physiological activator of trypsinogen and cleaves with high specificity after the sequence $(Asp_4)$—Lys (SEQ ID NO: 24). Light et al., J. Protein Chem. 10:475–480 (1991). It is possible to engineer the fusion protein to include a linker DNA sequence encoding the amino acid sequence recognized by enterokinase. See for example, Bollen et al., U.S. Pat. No. 4,828,988 (May 9, 1988); Rutlet, U.S. Pat. No. 4,769,326 (Sep. 6, 1988); and Mayne et al., U.S. Pat. No. 4,745,059 (May 17, 1988). However, although extensive research efforts have been mounted by several different research groups since the first partial purification of bovine enterokinase more than 15 years ago, no one has yet been successful in cloning enterokinase. Porcine enterokinase was first isolated in the early 1970s (Maroux et al., J. Biol. Chem. 246:5031(1971))and bovine (Anderson et al., Biochemistry 16:3354(1977)) and human (Grant et al., Biochem. J. 155:243(1976)) enterokinases were isolated in the late 1970s. Liepnieks et at., J. Biol. Chem. 254: 1677(1979) described an enterokinase having 35% carbohydrate, a molecular weight of 150,000, with a heavy (115,000) and light (35,000) chain connected by one or more disulfide bonds. Subsequent studies oft he light chain, i.e., the catalytic subunit, were reported in Light et al., J. Biol. Chem. 259:13195(1984). Most recently, Light et el., J. Protein Chem. 10:475(1991), disclosed what was later proven to be an incorrect partial amino-terminal sequence for the catalytic subunit of bovine enterokinase. To date, it has been impossible to obtain recombinantly produced enterokinase activity and there continues to exist a need for such a product.

BRIEF SUMMARY

The present invention provides novel purified nucleic acid sequences encoding enterokinase activity. Specifically provided is mammalian enterokinase activity, including human and bovine enterokinase and comprising the nucleic acid sequence as set forth in SEQ ID NO: 1, encoding the catalytic light chin, as well as portions of the heavy chain. The sequence comprises 2581 nucleotides and includes the catalytic domain, i.e. , nucleotides 1691 to 2398. A nucleotide sequence encoding this enterokinase activity and contained in the plasmid designated pEK-2/GI734 was deposited with the American Type Culture Collection (ATCC) on Feb. 2, 1993 and accorded the accession number 69232. In a further embodiment, the invention comprises the expression products of the novel sequences having enterokinase activity.

Nucleic acid forms such as genomic DNA (gDNA), complementary DNA (cDNA), and DNA prepared by de novo chemical synthesis from nucleotides, as well as DNA with deletions or mutations, allelic variants and sequences that hybridize thereto under stringent conditions (or which would hybridize but for the redundancy of the genetic code) are also within the contemplation of the invention so long as they encode polypeptides having enterokinase activity as defined below. Also, forms which contain modifications of the catalytic site of enterokinase which may allow for alteration of the specific cleavage site recognized by the enzyme are included. Further provided are novel messenger RNA (mRNA) sequences corresponding to these DNA sequences.

Association of nucleic acid sequences provided by the invention with homologous or heterologous species expression control sequences, such as promoters, operators, regulators, and the like, allows for in vivo and in vitro transcription to the corresponding mRNA which, in turn, allows translation of proteins and related poly- and oligopeptides, in large quantities, having enterokinase activity. In a presently preferred expression system of the invention, enterokinase encoding sequences are operatively associated with a regulatory promoter sequence allowing for transcription and translation in a eukaryotic cell system to provide e.g., enterokinase polypeptides having protease activity. The novel nucleic acid sequences may optionally encode both the heavy chain and the light chain of enterokinase, or the light chain alone which surprisingly still provides enterokinase activity. The enterokinase activity of the invention may be generated from one or more expression vector(s) each comprising one or more portions of the enterokinase activity, or, alternatively, the enterokinase activity can be generated from one or more expression vector(s) contained in one or more cell lines, each of which express all or a portion of the enterokinase activity. Thus, the heavy and light chains may be separately expressed in separate cell lines if desired. In addition, the enterokinase activity can be produced as a fusion protein, e.g., Using thioredoxin as the fusion partner. Optionally, the fusion partner can be all or part of yet another proteolytic enzyme, such as PACE, trypsinogen, and the like. Indeed, such an enterokinase fusion protein can contain an enterokinase cleavage site between the component protein domains, thereby allowing autocatalytic processing to separate the two domains and to yield mature, active enterokinase.

Incorporation of these sequences into prokaryotic and eukaryotic host cells by standard transformation and transfection processes, is also within the contemplation of the invention and is expected to provide useful enterokinase in quantities greatly in excess of those obtainable from tissue sources. The use of appropriate host cells provides for such post-translational modifications, e.g., truncation, glycosylation, etc., when needed to confer optimal biological activity on the expression products of the invention. Such appropriate host cells can include for example E. coli, CHO, yeast, and lepidoptera cells.

Novel protein products of the invention include those having the primary structural conformation (i.e., amino acid sequence) of enterokinase comprising the sequence substantially as set forth in SEQ ID NO:2 and having enterokinase protease activity. A presently preferred embodiment comprises the amino acid sequence substantially as set forth in SEQ ID NO:2 and specifically comprising amino acids 564 to 798. Antibodies to such products are also provided.

Also provided by the invention are methods for cleaving fusion proteins utilizing the novel protein products of the invention. These protein products can include both heavy and light chains or can be solely light chain enterokinase activity. Light chain alone is a "soluble" form of the enterokinase activity and is devoid of the non-enzymatic heavy chain which is believed to act as a membrane anchor in vivo. Surprisingly, while this form (light chain alone) of enterokinase is a poorer enzyme on trypsinogen, it is much more effective on fusion proteins. Provided also is a production method wherein one of the fusion protein members is itself enterokinase activity, which, upon cleavage of the fusion protein domains at a strategically located enterokinase recognition site, yields additional enterokinase activity at each round of cleavage to cleave more fusion protein.

Methods and pharmaceutical compositions are also provided for treating digestive disorders associated with low levels of enterokinase activity by administering the novel protein products of the invention.

Other aspects and advantages of the present invention will be apparent upon consideration of the following detailed description thereof which includes numerous illustrative examples of the practice of the invention.

BRIEF DESCRIPTION OF THE DRAWING

FIGS. 1, 1A, and 1B (SEQ ID NO: 1) provides the 2581 nucleic acid sequence and FIG. 2 (SEQ ID NO: 2) provides the predicted amino acid sequence of a portion of the non-catalytic domain (heavy chain) and the entire catalytic domain (light chain) of bovine enterokinase. Light chain is encoded by nucleotides 1691 to 2398 (amino acids 564 to 798) and the C-terminal portion of enterokinase heavy chain extends from nucleotides 1 to 1690.

DETAILED DESCRIPTION

The present invention provides recombinantly produced enterokinase activity, as well as methods of making and methods of using enterokinase activity. As used herein, enterokinase activity means the capability of cleaving peptide or protein substrates at a specific site; for protein substrates, this is generally following the sequence (Asp)$_4$—Lys (SEQ ID NO: 34), or a similar sequence such as those described in Light et at., Anal. Biochem. 106:199 (1980); (a cluster of negatively charged amino acids followed by a positively charged amino acid). Typically, such activity is measured by activation of trypsinogen by cleaving the N-terminal propeptide (containing (Asp)$_4$—Lys) (SEQ ID NO: 34) with enterokinase and subsequently assaying the amount of active trypsin generated using tosyl-argininemethylester (TAME). See, e.g., Maroux et al., supra. Alternatively, enterokinase activity can be measured directly by incubating the enzyme with the peptide substrate Gly—(Asp)$_4$—Lys—β-naphthylamide (SEQ ID NO: 35) and measuring the increase in fluorescence (excitation at 337 nm, emission at 420 nm) generated by cleavage and release of the β-NA(β-naphthylamide) moiety. See, e.g., Grant et at., Biochem. Biophys. Acta. 567:207(1979). Bovine enterokinase is also active on some trypsin substrates like TAME and BAEE (benzyl-arginine-ethyl-ester).

While it is generally assumed that optimal activity derives from holoenzyme, i.e. , the two-chain, heavy and light form of the enzyme, Applicants' invention also provides a proteolytic activity that derives solely from the light chain. Thus, as used herein, the term enterokinase activity does not require the presence of both heavy and light chains and can be derived solely from light chain.

Moreover, the chains or regions of the chains need not be the expression product of one vector, rather they can be separately and individually expressed. As used herein the terms co-transfection or co-expression are meant to include processes where the relevant nucleic acid sequences encoding the heavy and/or light chain(s) may be on a single or on one or more separate transfection or expression vector(s). Co-transfection and co-expression may employ one or more heavy and/or light chain sequences or may employ sequences having deletions from and/or mutations in the sequences but which still encode an enterokinase activity as described above.

In one embodiment of the invention, the enterokinase activity is the protein encoded by the nucleotide sequence set forth in SEQ ID NO: 1 and includes the mature catalytic domain, i.e. , nucleotides 1691 to 2398. As used herein, the term "a sequence substantially as" set forth in a SEQ ID NO is meant to encompass those sequences which hybridize to the sequence under stringent conditions as well as those which would hybridize but for the redundancy of the genetic code. Stringent conditions are generally 0.2. X SSC plus 0.1% SDS at 65° C. The terms "substantially duplicative" and "substantially corresponding" are meant to include those sequences which, though they may not be identical to those set forth in a SEQ ID NO, still result in expression product, proteins, and/or synthetic polypeptides that have enterokinase activity. Thus, using the nucleotide sequence as set forth in SEQ ID NO:1, DNA encoding enterokinase activity can be isolated and cloned from other sources as well using appropriate vectors, selectable markers and recombinant DNA techniques. The corresponding cDNA can be prepared from appropriate mRNA sources. Genomic DNA encoding enterokinase activity may also be obtained from a genomic library using a cDNA probe or oligonucleotide probes. Alternatively, an enterokinase activity-encoding DNA sequence may be prepared synthetically. The use of intronless, e.g. , cDNA sequences, are preferred, as bacterial expression requires intron-less sequences. The sequence may also be modified appropriately for expression in bacteria as described, supra.

The present invention also provides a method for producing enterokinase activity preferably in non-glycosylated form. The method involves culturing a host cell, preferably bacterial, transformed with (i.e., containing and capable of expressing) a DNA sequence encoding the enterokinase activity which is under the expression control of suitable transcriptional control sequences. The DNA sequence may encode both the heavy and light chains, or only light chain, or only as much as is required to result in the expression of enterokinase activity and may be deliberately designed to include preferred codons for expression in bacterial cells as is well known in the art. In the latter case, the resulting expression product of such deliberately designed DNA sequences may contain full length and may also contain a truncated, biologically active, mature peptide sequence encoding enterokinase activity, e.g., light chain alone.

In another preferred method for expression of enterokinase activity, the DNA sequence encoding the catalytic domain of enterokinase is fused to a signal peptide (pre-region) and pro-region of a gene, such as the human PACE gene. PACE is a serine protease which cleaves after dibasic residues and is responsible for propeptide processing of a number of secreted proteins. When the PACE signal peptide (pre-region) and pro-region coding sequence is fused in-frame to the mature enterokinase light chain coding sequence and expressed in mammalian cells, e.g., CHO cells, COS cells, BHK cells, and the like, the sequence is translated to produce a chimeric protein which is secreted and which is then processed to remove the signal peptide thereby yielding pro-enterokinase; subsequent cleavage, by either endogenous or exogenous PACE, removes the pro-peptide from the N-terminus of the enterokinase and mature enterokinase activity is secreted into the conditioned medium. Optionally, as a source of PACE, this method may employ co-expression of a modified, soluble form of the PACE gene having the transmembrane domain of PACE deleted. See, for example, Hatsuzawa et al., J. Biol. Chem. 267:16094(1992) for a description of soluble PACE and delineation of the pro-peptide portion of the protein. Other pre/pro regions can also be used to similar advantage in expressing enterokinase activity, for example, the pre/pro region of yeast Kex2 as described in Brenner et. al., Proc. Natl. Acad. Sci. U.S.A. 89:922(1992), or the pre/pro region of trypsinogen as described in LeHeuron et al., Eur. J. Biochem. 193:767(1990).

As used herein, the term "pro-protein" means a protein having attached to it a "pro" region; a "pre-pro-protein" has a "pre-pro" region attached to it. The "pre" region, or signal peptide, refers to the most N-terminal stretch of amino acids which target the remaining portion of the polypeptide to be translocated across a membrane, e.g., the endoplasmic reticular membrane, and is usually subsequently cleaved by an endogenous signal peptidase.

The "pro" region is an intervening region between the signal peptide (pre-region) and the mature protein. This sequence may be responsible for enhancing some post-translational modifications; it may be necessary for proper folding, or it may act to inhibit the activity of the mature protein until it is removed post-translationally. The pro region is usually removed after signal peptide cleavage by an endoprotease. A "pre/pro" region is a combination of the "pre" region and the "pro" region as described above. More specifically, useful DNA constructs include fusions of DNA encoding enterokinase activity with the pre/pro region of trypsinogen. The signal peptide and the entire 8 amino acid pro region of bovine anionic trypsinogen (which includes an enterokinase recognition site) is fused to the amino terminus of the mature enterokinase catalytic domain. Yet another DNA construct involves fusion of the mature enterokinase catalytic domain to the C-terminus of *E. coli* thioredoxin, having an intervening spacer sequence encoding a known cleavage site such as an enterokinase cleavage site.

The DNA sequence encoding enterokinase activity may be inserted by conventional methods into an expression vector suitable for the desired host cell as is well known in the art. For bacterial or yeast production, the DNA sequence should not contain introns. For higher eukaryotic expression, it is not necessary to avoid introns, but cDNA sequences are preferred. Preferably for eukaryotic expression, the DNA sequence should contain a secretory leader sequent. The vectors should contain typical vector elements well known in the art including replication sites, selectable markers and transcriptional control sequences compatible with the chosen host.

Various strains of *E. coil* useful as host cells for the production of non-glycosylated, homogeneous enterokinase activity are also well-known in the art. A non-exclusive list of such strains includes MC1061, DH1, RR1, C600hfl, K803, JA221, HB101, JM101 and various K12 strains, including the strain us the Examples. Alternatively, other bacterial species may be used, including *B. subtilis*, various strains of Pseudomonas, other bacilli and the like.

Enterokinase activity may also be produced by heterologous expression of an enterokinase activity encoding sequence in mammalian cells. Enterokinase activity is thus obtainable in glycosylated form, that is, unless glycosylation is prevented. Where desired, glycosylation can be inhibited by tunicamycin or by site-directed mutagenesis of gylcosylation sites, as is well known in the art. Suitable mammalian expression vectors and host cells for production of enterokinase activity are also well known in the art and include, without limitation, the vectors pXM and pMT2 and Chinese hamster ovary (CHO) cells, monkey COS-1 cells, CV-1, HeLa, mouse L-929, 3T3 cells and BHK cells. The construction and use of some exemplary mammalian vectors and cell lines is well known to those skilled in the art and is discussed in detail in WO 88/00598.

Many strains of yeast cells, known to those skilled in the art, are also available as host cells for expression of the enterokinase activity of the present invention. Yeast cells are especially useful as a host for the PACE pre/pro fusion to mature enterokinase as described above. When expressed using a suitable yeast vector, the fusion is secreted by virtue of the PACE signal peptide, and the PACE pro region is subsequently processed by the endogenous yeast protease KEK2, an enzyme homologous to human PACE which also cleaves after paired basic residues. Additionally, where desired, insect cells may be used as host cells. See, for example, Miller et al, Genetic Engineering 8:277–98 (Plenum Press 1986) and references cited therein.

When the enterokinase activity of this invention is expressed in bacterial cells, it may be expressed intracellularly usually without regard to refolding since that is typically unnecessary to obtain the protein in active form, or it may be secreted from bacterial cells in active form, if a secretory leader is included. Where necessary or desired, as when reduced bioactivity is observed, the enterokinase activity product may be refolded by conventional methods such as incubation of protein in urea or guanidine HCl with dithiothreitol or β-mercapto ethanol, followed by dilution to reduce the concentration of these reagents and treatment with oxidizing agents.

For example, *E. coli* cells, genetically engineered to express an enterokinase activity DNA sequence as described herein, are cultured under suitable conditions permitting the production and intracellular accumulation of enterokinase activity protein. The cells are then harvested, i.e., separated from the medium in which they were cultured and from any other materials, and lysed and the desired biologically active enterokinase activity protein is purified from the lysate. Optionally, only minimal purification of the enterokinase activity is required.

The term "biologically active" means a preparation of enterokinase activity that exhibits a detectable level of proteolytic cleavage activity as assayed by conventional methods discussed, supra. Various purification techniques, such as column chromatography (e.g., ion exchange, immunoaffinity, etc.), affinity purification on soybean trysin inhibitor (STI), pancreatic trypsin inhibitor (PTI) or PABA, gel filtration and reverse phase HPLC, are useful in purifying the desired protein. See, for example, Gospodarowicz et al., J. Cell. Phys 122:323–32(1985), Iwane et al., Biochem. and Biophys. Res. Comm. 146:470–77(1987), Fox et al., J. Biol. Chem. 265:18452–58(1988), EP 0 259 953 published Jun. 4, 1987, and EP 0 237 966 published Sep. 23, 1987.

The enterokinase activity of the invention can be used in a method for cleaving protein having an enterokinase cleavage site, and especially fusion proteins having such a cleavage site engineered into their sequence. The amounts needed are readily determined empirically by one skilled in the art. Indeed, as described herein, recombinant bovine enterokinase catalytic domain is a superior reagent for cleavage of fusion proteins when compared to the bovine-derived two-chain form, as it is much more efficient and is not contaminated with trace amounts of other proteolytic proteins which are difficult to remove. As another aspect of the invention, the enterokinase activity of the invention is incorporated as one of the fusion protein partners to yet another protein. As such, with the addition of a minimal amount of exogenous enterokinase activity to the reaction vessel (or by merely concentrating the fusion protein adequately), a minimal amount of cleavage of the fusion protein results in the release of additional enterokinase activity which in turn can catalyze many more proteolytic cleavages of fusion proteins. In this way, large amounts of enterokinase activity can be produced from a fusion protein in an autocatalytic manner. Also provided by the invention is a method for producing proteins from fusion proteins which comprises the steps of:

(a) growing, in culture, a host cell transformed or transfected with (i) a nucleic acid which encodes enterokinase activity and which upon expression is segregated into the periplasmic space; and (ii) one or more nucleic acids which encode a fusion protein and an enterokinase cleavage site and which, upon expression are segregated to the cytoplasmic space, (b) allowing said periplasmic space and said cytoplasmic space to co-mingle thereby, (c) allowing said enterokinase activity to cleave said fusion protein, and (d) resulting in protein production.

Pharmaceutical compositions containing the homogeneous enterokinase activity of the present invention may be useful as digestive agents. Such pharmaceutical compositions may also contain pharmaceutically acceptable carriers, diluents, fillers, salts, buffers, stabilizers and/or other materials well-known in the art. The term "pharmaceutically acceptable" means a material that does not interfere with the effectiveness of the biological activity of the active ingredient(s) and that is not toxic to the host to which it is administered. The characteristics of the carrier or other material will depend on the route of administration. Administration can be carried out in a variety of conventional ways. Oral administration is preferred. In such case, the enterokinase activity of the present invention can be enterically coated, the preparation of which is within the skill in the art. In practicing the method of treatment of this invention, a therapeutically effective mount of enterokinase activity is administered. The term "therapeutically effective amount" means the total amount of each active component of the method or composition that is sufficient to show a meaningful benefit, i.e., restoration of digestive function. When applied to an individual active ingredient, administered alone, the term refers to that ingredient alone. When applied to a combination, the term refers to combined amounts of the active ingredients that result in the therapeutic effect, whether administered in combination, serially or simultaneously. The number of applications may vary, depending on the individual and the severity of the digestive disorder. In yet another method of use, it is contemplated that the DNA encoding enterokinase would be useful in gene therapy as a means of correcting digestive disorders due to enterokinase deficiency.

The invention is further described in the following examples, which are intended to illustrate the invention without limiting its scope. Example 1 describes the cloning of a 26 bp bovine enterokinase gene fragment. Additional protein sequencing of bovine enterokinase is described in Example 2. The amplification and cloning of a gene fragment adjacent to the Example 1 fragment is the subject of Example 3. Example 4 relates to the cloning of the enterokinase catalytic chain. A comparison of the different cDNA clones, as well as a partial coding sequence for the non-catalytic (heavy) chain is set forth in Example 5. Example 6 describes the isolation of additional enterokinase coding sequence including additional heavy chain sequence. Example 7 describes the use of the bovine enterokinase sequence to clone other mammalian enterokinase genes. Example 8 describes the expression of a gene encoding the catalytic domain of bovine enterokinase in both a procaryotic cell system as well as in a eukaryotic cell system. Example 9 relates to the co-expression of fusion proteins and to the production of active enterokinase. Example 10 relates to the use of enterokinase as a therapeutic agent in the treatment of certain digestive disorders.

EXAMPLE 1

Cloning of a Bovine Enterokinase Gene Fragment

A purported N-terminal 27 amino acid sequence of the catalytic (light) chain of bovine enterokinase was provided by Albert Light of Purdue University and was later published in Light et al., supra. As discussed in greater detail, infra., this sequence was incorrect. Because of the error, the tyrosine reported at position 8 was used in designing probes and primers due to its low degeneracy (only two possible codons encode tyrosine). However, the actual residue at position 8 is in fact arginine, with six possible codons. This (erroneous) sequence is as follows:

SEQ ID NO:3
```
1          10            20        27
I V G G S D S Y E G A W P W V V A L--Y F D D Q-Q V C G
```

The "provided" sequence was backtranslated into all possible DNA codons which it could encode, and was used to design pools of oligonucleotide primers 17 base pairs in length with 5' extensions to encode restriction endonuclease cleavage sites to be used as primers in PCR reactions [Saiki et el., Science 250:1350–1354(1985); Mullis et al, Cold Spring Harbor Symposia on Quantitative Biology, Vol. LI:263–273(1986)]. The design of these oligonucleotide pools was critical to the potential success of the endeavor. Comparison of this N-terminal protein sequence to previously identified sequences in the databases revealed significant homology to a large number of mammalian pancreatic and serum serine proteases. To prevent unwanted amplification of DNA sequences encoding these "unwanted" proteins, the PCR primer pools were designed to intentionally avoid these highly homologous regions. However, the competing requirement of spacing the sequences to which the primer pools anneal as far apart as possible, was taken into account to maximize the amount of exact enterokinase sequence generated for the amplification to provide useful information.

Two degenerate oligonucleotide pools, which together contained all possible codons for the N-terminal amino acid sequence: IVGGSD (amino acids 1-6) SEQ ID NO:8, were synthesized. These two pools differed only in the codons used for the serine residue in the protein sequence and were used independently as a means of decreasing the degeneracy of each pool:

SEQ ID NO:4
PRIMER 1A 5' CTCGAATTCATHGTNGGNGGNTCNGA 3' 768x and

SEQ ID NO:5
PRIMER 1B 5' CTCGAATTCATHGTNGGNGGNAGYGA 3' 384x

As used herein, the symbol "H" refers to equal proportions of nucleotides C, T, and A. The symbol "Y" refers to equal proportions of nucleotides C and T. "R" refers to equal proportions of either A or G at that position. The symbol "N" refers to equal proportions of the four nucleotides G, A, T, and C. Each of these pools had a 5' extension which contained an EcoRI site which is shown in bold print.

Another pool of oligonucleotides was synthesized which contained the reverse complement of all possible codons for the most C-terminal known sequence:

DQQVCG (amino acids 22–27 of SEQ ID NO:3). SEQ ID NO:6

This pool contained a common 5' extension shown in bold which contained a HindIII site:

SEQ ID NO:7
PRIMER 2 5' TCCAAGCTTCCRCANACYTGYTGRTC 3' 64x

The DNA products from the first series of amplification reactions were used as the template for a second series of amplifications primed by oligonucleotide pools which are complementary to the inferred DNA coding sequence of amino acids "interior" to the first set in the linear sequence. Thus, a pool of 17 base pair oligonucleotides complementary to all possible codons for the sequence:

(SEQ ID NO:8
YEGAWP (which corresponds to amino acids 8–13 of SEQ ID NO:3, including the incorrect assignment of Y at position 8) was synthesized:

PRIMER 3 5' TAYGARGGNGCNTGGCC 3' 64x    SEQ ID NO:9

This pool of primers was then combined in the second PCR reaction with another pool comprising the reverse complement of all possible codons for the sequence:

SEQ ID NO:10
FDDQQV (corresponds to amino acids 20–25 of SEQ ID NO:3)

SEQ ID NO:11
PRIMER 4 5' TCCAAGCTTACYTGYTGRTCRTCRAA 3' 32x

This pool has partial overlap with the 3' pool used in the first series of amplifications, and contains a 5' extension (in bold) which includes a HindIII site.

Bovine genomic DNA (0.9 mg/ml in dH$_2$O) was boiled for 5 minutes to denature and was then immediately placed on ice. Reaction conditions for each 50 μl amplification reaction were: 2 μg heat denatured bovine genomic DNA, 10 mM Tris-Hcl pH 8.3, 50 mM KCl, 1.5 mM MgCl$_2$, 0.01% gelatin, 1.0 μM of each oligonucleotide pool, 200 μM of each dNTP, and 1 unit of Amplitaq, a Thermus aquaticus DNA polymerase (Perkin-Elmer Cetus). Forty amplification cycles were run under the following conditions: cycle 1=94° C., 3 minutes/40° C., 1 minute/72° C., 1 minute. Cycles 2–40=94° C., 1 minute/40° C., 1 minute/72° C., 1 minute. The first round of 40 cycles utilized either primer pools 1A and 2 or pools 1B and 2. After 40 cycles of amplification, 0.5 μl of this reaction was used as template for a second 35 cycles of PCR using primer pools 3 and 4. The conditions for this round of 35 PCR cycles were 94° C., 1 minute/35° C., 2 minutes/72° C., 2 minutes. Reaction components were the same as the first round except for the DNA template. The DNA template in the second round was the product of the previous round.

PCR products obtained as described above, were run on 5% acrylamide preparative gels, and bands were stained with 0.5 μg/ml ethidium bromide, excised from the gel and electroeluted. DNA manipulations and ligations were performed using standard techniques [Sambrook et al., in "Molecular Cloning, a Laboratory Manual," second edition, Cold Spring Harbor Laboratory Press. (1989)]. PCR products were first treated with Klenow fragment of DNA polymerase I in the presence of all four deoxynucleotide triphosphates, then digested with HindIII (New England Biolabs) and subcloned into a pUG19 [Norrander et al., Gene 26:101–106(1983)] HincII-HindIII vector. Transformants were identified which contained plasmids with an apparent insert of approximately 72 bp. These plasmids were isolated and their inserts were sequenced using the Sequenase kit (United States Biochemical) and a sequencing primer which anneals to pUC19. The DNA sequence of the inserts was then translated to reveal an open reading frame which corresponded exactly to the amino acid sequence predicted by the known protein sequence (WVVALY, amino acids 14–19 of SEQ ID NO:3). Due to the possibility of mismatch tolerance during primer annealing, only the sequence between the two PCR primers could be assumed to be correct. However, it was assumed that the proper serine codon was in primer pool 1B (AGY), as the other pool (1A) failed to yield a specific product; this was determined by Southern blot of product from the first 40 cycles, probed with pool designated SEQ ID NO:9. Also, since the "wobble" position of the codon for Pro$^{13}$ was determined to be a thyroidine, and there is only one possible codon for the adjacent Trp$^{12}$, 5 additional bases were also assumed to be fairly certain. When the first two invariant bases of the codon for Phe$^{20}$ are included, 26 contiguous base pairs of coding sequence for nine amino acids of the enterokinase catalytic chain (amino acids Trp$^{12}$ to Phe$^{20}$) had been determined with a fair degree of certainty. This sequence is nucleotides 1724 to 1749 of SEQ ID NO: 1.

EXAMPLE 2

Protein Sequencing of Bovine Enterokinase

The exact DNA sequence (26 bp) of amino acids 12–20 of mature bovine enterokinase light chain was not sufficient to allow cDNA isolation by a hybridization approach. Accordingly, additional adjacent protein sequence was sought.

Bovine enterokinase (EK-2 grade) was purchased from Biozyme. The enzyme was greater than 99% impure, thus the enzyme was further purified using porcine pancreatic trypsin inhibitor (Sigma) coupled to activated SEPHAROSE CL-4B (Sigma) [Liepnieks et al., I. Biol. Chem. 254:1677–1683(1979)]. The resulting enzyme was reduced and alkylated to separate the heavy chain from the light chain and run on a preparative acrylamide gel. The proteins were electroblotted from the gel onto a Problot, a polyvinylidene fluoride membrane Polyvinylidene Elueria membrane (Applied Biosystems, Inc.), and the catalytic chain of M 42,000 daltons was excised from the membrane after staining and was sequenced using an APPLIED BIOSYSTEMS MODEL pulse liquid sequencer. The sequence for the first 30 amino acids was determined and is:

SEQ ID NO:12
```
1           10           20           30
I V G G S D S R E G A W P W V V A L Y F D D Q Q V C G A S L
```

Of particular note is the observation that the amino acid residue in the 8th position was determined to be an arginine, in contrast to the tyrosine incorrectly reported by Light et al., supra. This is a crucial area of the sequence for designing PCR primers due to its reported low degeneracy.

Two additional bands were observed upon electoblotting. The expected heavy chain band at $M_r$ 150,000 daltons and another band at $M_r$ 90,000 daltons were excised from the Problot, a polyvinylideae fluoride membrane, treated individually with trypsin, and the resulting fragments separated on reverse phase. Well-separated peaks were collected and sequenced.

The reduced and alkylated bovine enzyme was also run on a C4 reverse phase column (Vydac) to separate the non-catalytic (heavy) chain from the catalytic (light) chain. The peak corresponding to the catalytic chain was treated with TPCK-trypsin (Worthington). The resulting trypile peptides were separated on C18 reverse phase HPLC (Vydac). Individual peaks were subjected to sequence analysis on the protein sequencer. The results are presented in Example 3.

EXAMPLE 3

Amplification and Cloning of an Adjacent Gene Fragment

Tryptic digestion and chromatographic separation and isolation of individual peptide fragments of enterokinase catalytic chain, followed by subsequent sequencing of each resulting peptide, resulted in the following sequences:

| | |
|---|---|
| EGAWPWVVALYFDDQQVCGASLVS | SEQ ID NO:13 |
| DWLVSAAHCVYGR | SEQ ID NO:14 |
| FTEWIQSFLH | SEQ ID NO:15 |
| ICSIAGWGALIYQGSTADVLQEA | SEQ ID NO:16 |
| WLLAGVTSFGYQCALPN(N?)PGVYA | SEQ ID NO:17 |
| NMEPSK | SEQ ID NO:18 |

SEQ ID NO: 13 is a 24 residue peptide that partially overlapped with the N-terminal sequence as determined in Example 2. These peptide sequences were used to search protein sequence databases for homology. The protein which displayed the highest degree of sequence homology to the N-terminal peptide sequence of enterokinase was an inferred amino acid sequence from a human liver cDNA done, named hepsin [Leytus et al., Biochemistry 27:1067–1074(1988)]. Using the hepsin sequence as a guide, another enterokinase catalytic chain tryptic peptide (SEQ ID NO:14) appeared it might be contiguous with the N-terminal/overlapping tryptic sequence already identified. This peptide contained a sequence highly homologous to the histidine region of the "catalytic triad" which is characteristic of serine proteases. Oligonucleotide pools which were complementary to the reverse complement of the backtranslated amino acid sequence for a region of this (amino acid 7 to 11 of SEQ ID NO:14) peptide, AHCVY, were synthesized. These oligos also contained a 5' extension (shown in bold) which encodes a BamHI site:

SEQ ID NO:19
PRIMER 5 5' CGCGGATCCCCRTANACRCARTGNGC 3' 128x

This pool was used for genomic DNA PCR in combination with the other oligonucleotide pools and also with oligonucleotides containing the 19 base pairs (and the reverse complement) of exact enterokinase DNA sequence (nucleotides 1729–1747) from the first PCR clone in Example 1, along with 5' restriction site extensions, as shown below:

| | |
|---|---|
| CCGGAATTCTTGGGTCGTTGCTCTGTAT | SEQ ID NO:20 |
| CGCGGATCCATACAGAGCAACGACCCAA | SEQ ID NO:21 |

A nested approach was again utilized on bovine genomic DNA. The following combinations proved fruitful:

1) SEQ ID NO:5+7, 40 cycles followed by SEQ ID NO:5+21, 35 cycles
2) SEQ ID NO:5+19, 40 cycles followed by SEQ ID NO:20+19, 35 cycles Combination 1, after subcloning and sequencing, yielded 21 bp of sequence (5 bp of which had previously been determined) which translated to $Asp^6$ to $Pro^{13}$ of the enterokinase light chain peptide sequence SEQ ID NO: 12, and the inferred remaining two bases of the $Asp^6$ codon to total 23 bp. This DNA sequence corresponds to nucleotides 1706 to 1728 of SEQ ID NO:1 and confirmed that residue #8 was indeed an arginine and not a tyrosine as had been incorrectly reported by Light et al., supra.

Likewise, combination 2 yielded 60 bp of sequence (2 bp of which had previously been determined) which translated to $Phe^{20}$ to $Ala^{40}$ of the enterokinase light chain N-terminal protein sequence (SEQ ID NO:12) and the overlapping tryptic peptide sequence (SEQ ID NO:13) and showed that adjacent peptide SEQ ID NO:14 begins with residue 34. The residue at position 33, which was undetermined from protein sequencing but was presumed to be a basic residue responsible for the tryptic hydrolysis, was determined to be an arginine from the coding sequence. When the sequences for all three PCR products were combined, a total of 104 bp of exact, contiguous coding sequence had been determined for $Asp^6$ to $Ala^{40}$ (and the first two bases of the codon for $Ala^{41}$) of the catalytic chain of bovine enterokinase. With this sequence information in hand, only now was it possible to attempt to clone the catalytic domain of enterokinase with any reasonable chance of success.

EXAMPLE 4

Cloning of Enterokinase Catalytic Chain

Two separate bovine small intestine cDNA libraries were used for the cloning of the gene for the enterokinase catalytic domain. PCR was performed on λ libraries of bovine liver and small intestine cDNA's using exact primers designed to this newly determined nucleotide sequence as described supra, in Example 3. cDNA from bovine liver gave a very weak product implying that the abundance in the library was very low, while the small intestine library yielded much more specific product. Thus bovine small intestine was chosen as a possible mRNA source. The first cDNA library was a λ gt10 library which was purchased from Clontech. The second cDNA library, referred to as the Lambda Zap library, was prepared as follows. Bovine duodenal tissue was obtained and mRNA was prepared from a portion of the tissue using the guanidinium extraction method [Chirgwin et at., Biochemistry 18:5294(1979)]. Oligo (dT)-primed cDNA was synthesized using standard techniques [Sambrook et al., supra.]. Synthetic NotI/EcoRI adapters (Invitrogen) were ligated to the resulting cDNA, which was then ligated into Lambda Zap II Eco RI arms (Invitrogen).

Recombinant phage from either cDNA library were hybridized, in duplicate, to two separate oligonucleotides whose sequences were complementary to the enterokinase DNA sequence determined from the subcloned PCR fragments of Example 3. The first oligonucleotide was 21 bases in length and comprised the plus strand of the coding sequence for $Asp^6$ to $Trp^{12}$. The second oligonucleotide was 20 bases in length and comprised the minus strand of the coding sequence for residues $Asp^{35}$ to $Ala^{41}$.

The oligonucleotides were labelled using $[^{32}P]$-λATP and polynucleotide kinase [Sambrook et al., supra.]. Hybridizations were performed as described [Sambrook et al., supra.] using the following conditions: 6x SSC, 0.5% SDS, 5x Denhardt's solution, 10 mM $Na_2EDTA$, 100 μg/ml yeast RNA, and 0.1 pmole/ml labelled oligonucleotide. After hybridization for 16 hours at 60° C., filters were washed in 2xSSC, 0.1% SDS at room temperature 4 times for 15 minutes each time.

A single plaque containing sequences which hybridized to both of the oligonucleotide probes was isolated from $1 \times 10^6$ recombinant phage from the Clontech library. The sequence of the insert (called clone #3e) in this recombinant phage was 769 bp. The insert contained a long open reading frame which encoded several of the tryptic peptides previously sequenced: SEQ ID NO: 13,14 17, as well as a portion of SEQ ID NO: 16. The reading frame continued past the 3' end of the insert, suggesting that the clone was incomplete. In addition, the reading frame contained the IVGG- N-terminus (amino acids 1–4 of SEQ ID NO:3) predicted from the protein sequencing data. The reading frame remained open in the 5' direction for another 26 codons before terminating.

From the Lambda Zap II bovine small intestine cDNA library, $5 \times 10^5$ phage were screened by hybridization with the same two oligonucleotides as above. Only two recombinant phage were isolated which contained enterokinase-specific sequence complementary to the oligonucleotide probes. One of these (called clone #11) was 1494 base pairs long and contained all of the light chain coding sequence present in the cDNA clone from the Clontech library but differed 5' of the coding sequence for light chain. It also contained the remaining 3' coding sequence and almost 80 bases of 3' untranslated sequence. This clone also contained a significant extension of the open reading frame preceding the N-terminal IVGG of the mature catalytic chain, extending 266 codons and remaining open at the 5' limit of this clone (to nucleotide 893 of SEQ ID NO:1), which differed with clone 3e.

The second phage had an insert (called clone #22) which was considerably smaller, only 531 bp (SEQ ID NO: 1, nucleotides 1553–2068), the sequence of which was fully contained within the first clone. Of interest, however, were the final 21 codons of the open reading frame contained on clone #22 which were not present in either of the other two cDNA clones (SEQ ID NO: 1, nucleotides 2006–2101). Thus, it was unclear where this sequence fit in and/or whether it was merely a cloning artifact.

EXAMPLE 5

Comparison of Different cDNA Clones

Comparison of the Clontech library clone #3e with clone #11 revealed that the two sequences diverge at almost exactly the point at which the 5' open reading frame of clone #3e terminates. Examination of the DNA sequence surrounding this point reveals a potential mRNA splice site [Padgett et al., Ann. Rev. Biochem. 55:1119–1150(1986)], and leaves open the possibility that clone #3e contains an unspliced intron which interrupts the open reading frame (ORF). Further support for this possibility comes from the identification of a tryptic sequence:

LVTQEVSPK            SEQ ID NO:22 isolated from the 150,000 dalton protein fragment which matches the ORF sequence immediately preceding the IVGG N-terminal sequence of the mature catalytic chain in clone #11. This tryptic sequence is interrupted by divergent sequence in clone #3e. In addition, two other tryptic peptides:

A-FTTGYGLGIPEP            SEQ ID NO:23 and

LF-GTTDSSGLVQF            SEQ ID NO:24 isolated from the 150,000 dalton enterokinase protein band match two regions of the translated ORF of clone #11 upstream of the catalytic chain coding sequence. Therefore, this upstream ORF apparently represents the coding sequence for the non-catalytic (heavy) chain, which is believed to be generated from a single proteolytic cleavage immediately prior to the mature catalytic chain N-terminal sequence to separate the mature catalytic chain from the non-catalytic chain.

EXAMPLE 6

Isolation of Additional Enterokinase Coding Sequence

Nested oligonucleotide primers were synthesized which were complementary to the lambda DNA sequence adjacent to the cloning site for the cDNA insertions. These primers are shown as Lambda Primers below. In addition, primers were designed which are complementary to the plus strand of the most 5' region of the enterokinase coding sequence as described, supra. These primers are shown as EK Primers below. The innermost primers were designed to contain a 5' extension (shown in bold) to encode a restriction endonuclease cleavage site.

Lambda Primers

5' CTATAGACTGCTGGGTAGTCCCC 3' OUTER    SEQ ID NO:25

5' ATAAGAATGCGGCCGCAAGTTCAGCCTGGTTAAGTCCAAGC 3' INNER    SEQ ID NO:27

EK Primers

5' CCAAATACAGAAAGCCTGATTAGGG 3' OUTER    SEQ ID NO:27

5' GTAGGTCGACCGTGAATGTTGTATTTGGCTCCC 3' INNER    SEQ ID NO:28

Nested PCR was then performed as follows: each 100 μl reaction contained 1×10$^8$ recombinant phage from the Clontech bovine small intestine lambda gt10 cDNA library, 1 μmole of each outer primer, 200 μM dNTPs, and 1 unit of Amplitaq, a Thermus aquaticus DNA polymerase (Perkin-Elmer Cetus) in a final concentration of 10 mM Tris-HCl pH 8.3, 50 mM KCl, 1.5 mM MgCl$_2$. Thirty-five cycles were performed under the following conditions: 94° C., 1 minute; 65° C., 2 minutes; 72° C., 2 minutes. Five microliters were removed from this reaction and used as template for another 35 cycles utilizing the inner primers and the same reaction conditions. The products from this reaction were then run on a 1% polyacrylamide gel, stained in a solution of 0.5 μg/ml ethidium bromide and visualized under UV light. The resulting bands were excised, electroeluted, and digested with NotI and SalI prior to subcloning into a pBluescript Sk+™ (Stratagene) NotI/SalI vector. The resulting subclones were sequenced, and additional DNA sequence encoding another 116 amino acids of enterokinase heavy chain was determined. This new protein sequence contained regions corresponding to two additional tryptic peptides which had been isolated from the 150 Kd protein band, (LS) INISSDQNMEK [SEQ ID NO:29] and VSFYGFK [SEQ ID NO:30], and another from the 90 Kd protein band QKEG-NYGQNWNYGQVTLNET [SEQ ID NO:31]. In addition, two separate N-termini were sequenced from the 90 Kd band, and both are identified in this sequence: (VGLLTLP . . . )[SEQ ID NO:32] and (TIFQK . . . )[SEQ ID NO:33]. Thus, the 90 Kd protein band seen in reduced and alkylated bovine-derived enzyme may be a proteolyzed form of the heavy chain which rims at an apparent 150 Kd on these gels. These two N-termini both follow a basic residue, indicating that a trypsin-like enzyme may be responsible for proteolysis of the intact heavy to this smaller (90 kD) form.

Using the technique described above, the complete heavy chain sequence is obtained by repeating this method each time additional 5' coding sequence is identified. New nested PCR primers are designed to the most 5' sequence, and nested PCR with 1×10$^8$ recombinant phage from a bovine small intestine λ cDNA library is performed. Additional 5' enterokinase heavy chain coding sequence is thus amplified, subcloned, sequenced and the procedure repeated until the entire coding sequence has been identified and isolated.

EXAMPLE 7

Use of the Bovine Enterokinase DNA Sequence to Clone Other Mammalian Enterokinase Genes The determination of the DNA sequence of bovine enterokinase directly enables isolation and sequencing of the genes for the equivalent enzymes from numerous other mammalian species. The subject invention determined that the enterokinase gene is expressed in the duodenum, thereby eliminating the uncertainty of tissue sources for enterokinase mRNA regardless of species. This information provides assurance that cDNA made from duodenal mRNA will contain the enterokinase gene. Thus, expression libraries containing cDNA made from duodenal mRNA from virtually any mammalian species can be screened using antibodies to the particular enterokinase protein which is sought. Polyclonal antibodies to the bovine enzyme are useful for identification of enterokinase clones from expression libraries made from other species.

In addition, the cDNA sequence for the bovine enzyme can be used directly as a hybridization probe for other mammalian enterokinase genes, or can be used to design oligonucleotide probes useful for cloning enterokinase genes from cDNA or genomic libraries made from mRNA or genomic DNA of other species. It is reasonable to assume that the enterokinase catalytic domain protein sequence will be highly conserved among species due to the fact that it now appears that there is nearly absolute conservation of the substrate recognition sequence. Using the entire bovine enterokinase catalytic domain as a hybridization probe to screen cDNA or genomic libraries of other species at reduced stringency allows isolation of the desired enterokinase gene. Alternatively, oligonucleotides which encompass the DNA sequence encoding the regions surrounding the "catalytic triad", i.e., His$^{41}$, Asp$^{92}$, and Ser$^{187}$ are likely to be most highly conserved and most useful for cross-species hybridization.

EXAMPLE 8

Expression of the Gene Encoding the Catalytic Domain of Bovine Enterokinase

A. CHO Cell Expression

1. PACE

The DNA sequence encoding the catalytic domain (nucleotides 1691 to 2398) of bovine enterokinase, was fused in-frame to the 3' end of the DNA encoding the signal peptide and pro- region of the human PACE gene. PACE is a mammalian serine protease which cleaves after dibasic residues, and is responsible for propeptide processing of a number of secreted proteins. (Wise et al., Proc. Nat. Acad. Sci. USA 87:9378–9382(1990). When expressed in CHO cells, this sequence was translated to produce a chimeric protein which was secreted with subsequent signal peptide processing to yield pro-enterokinase. The PACE pro-peptide contains a sequence (—Arg—Thr—Lys—Arg—) (SEQ ID NO:36) at the C-terminal junction with mature enterokinase sequence; this is the cleavage site for the PACE enzyme. CHO cells also produce endogenous levels of PACE. During secretion of the PACE pro/enterokinase light chain, host PACE cleaved the pro-peptide from the N-terminus of the enterokinase, resulting in secretion of mature enterokinase catalytic domain to the conditioned media. Immunoprecipitation experiments using rabbit polyclonal antisera raised against bovine-derived enterokinase revealed a 42 Kd product was secreted into the conditioned media.

This conditioned media contained cleaving activity toward the fluorogenic enterokinase substrate Gly—(Asp$_4$)—Lys—βNA (SEQ ID NO:35) (Bachem Bioscience) (corresponding to approximately 50–500 ng/ml depending on the cell line). This activity was inhibited by the addition of either soybean trypsin inhibitor (STI,Sigma) or bovine pancreatic trypsin inhibitor (BPTI, Sigma). It has been reported that the bovine holoenzyme, i.e. , having both heavy and light chains, is inhibited by only BPTI and not STI, while the partially reduced and alkylated light chain is inhibited by both [Light et al., J. Biol. Chem. 259:13195–13198(1984)]. In addition, incubation of this conditioned media with a partially purified fusion protein of *E. coli* thioredoxin/human IL-11 which contains an interdomain spacer consisting of the enterokinase cleavage sequence (—Gly—Ser—Gly—Ser—Gly—[Asp$_4$]—Lys—Asn—) (SEQ ID NO:37) resulted in total and specific cleavage of this fusion protein into its two component domains (thioredoxin and IL-11), with cleavage occurring between the Lys and Asn residues in the spacer sequence. In addition, this CHO-produced recombinant enterokinase catalytic domain was capable of specifically cleaving other fusion proteins containing this same spacer, for instance an *E. coli* thioredoxin/human MIP-1α fusion and an *E. coil* thioredoxin/human MIF fusion, into their component parts. This cleavage was confirmed by SDS-PAGE analysis of the cleavage products.

The relative molar activities were as follows:

| EFFICIENCY OF CLEAVAGE | | |
|---|---|---|
| Substrate | Holoenzyme | CHO Produced Light Chain |
| Gly—(Asp4)—Lys—βNA (SEQ ID NO: 35) | 1 | 1 |
| Trypsinogen | 100 | 1 |
| Trx/IL-11 | 1 | 25 |

Quite surprisingly, the CHO-produced light chain is 25 times more effective than bovine-derived holoenzyme when used to cleave a thioredoxin/IL-11 fusion protein containing an enterokinase cleavage site between the two protein domains. This dramatic difference is duplicated on the other fusion proteins listed above. In addition, secondary proteolysis due to contaminating serine proteases (e.g. trypsin and chymotrypsin) which co-purify with bovine-derived holoenzyme is absent with the recombinant single chain form. As such, recombinant single chain enterokinase is a superior reagent for fusion protein cleavage.

2. Modified PACE

This expression system has been improved by co-expression of a modified version of the PACE gene which has had the transmembrane domain deleted. Rehemtulla et al., Blood 79:2349 (1992). This overexpressed and secreted PACE efficiently processes the PACE pre/pro-enterokinase and allows greater processing capability for enterokinase overexpression, as endogenous PACE levels in CHO cells are low and incapable of processing highly expressed pro-enterokinase. Thus, at high expression levels, endogenous PACE activity becomes limiting with some enterokinase remaining unprocessed and resulting in some inactive material. Increasing soluble PACE levels allow for the accumulation of high levels of properly processed, active enterokinase in the conditioned media.

3. Trypsinogen

Constructs were also prepared which fused the DNA encoding the pre/pro region of bovine anionic trypsinogen [Le Heurou et al., Eur. J. Bioehem. 193:767–773(1990)] in-frame to the DNA sequence encoding the mature enterokinase catalytic domain. The pro region of trypsinogen contains an enterokinase cleavage site (Asp$_4$—Lys) (SEQ ID NO:34) as it is the natural substrate of enterokinase, and this construct was designed to produce secreted enterokinase "zymogen" with the trypsinogen propeptide attached to its N-terminus which could then be activated by addition of enterokinase to initiate autocatalytic processing. Expression of this construct in CHO cells resulted in mostly intracellular accumulation; however, the small amount of material secreted gave undetectable levels of activity in a fluorogenic enterokinase peptide assay. In addition, activity was not stimulated by the addition of enterokinase to the proprotein. It appears that this chimeric protein is not capable of forming an active species. It is speculated that the light chain benefits from translational fusion with a large protein domain (analogous to heavy chain) which is post-translationally removed to allow the active conformation of light chain to form. The PACE pro-peptide functioned effectively in this capacity.

B. Expression In *E. Coli*

In an effort to increase solubility and produce enterokinase with an authentic N-terminus, the coding sequence for the catalytic chain was fused in-frame to the 3' end of the *E. coli* thioredoxin gene [Luna et al, J. Biol. Chem. 259:10469–10474(1984)] with a spacer which encodes an enterokinase cleavage site (—Gly—Ser—Gly—Ser—Gly—[Asp$_4$]—Lys) (SEQ ID NO:37). This construct is under the transcriptional control of the lambda pL promoter [Shimatake et al., supra.] on a multicopy plasmid, and directs the cytoplasmic expression of a thioredoxin/enterokinase catalytic domain fusion protein. A portion of the expressed fusion protein is soluble when expressed at 17° C., and full solubility can be achieved by lysing the cells in the presence of low levels of urea (e.g., 3M). This fusion protein can be purified from cell lysates and cleaved with enterokinase to generate active enterokinase. The intent of this construct is to allow autocatalytic processing of the fusion protein, i.e. , cleavage is begun by a small amount of active enterokinase (either holoenzyme or catalytic chain), and as active catalytic chain is released from its fusion partner it can then continue to cleave remaining fusion protein in the reaction. At least partial purification of the fusion protein is necessary to eliminate inhibitor(s) of enterokinase present in *E. coil* cell lysates. Active light chain, specifically inhibited by STI, is produced.

Alternatively, other fusion partners may also be employed. For instance, the *E. coli* maltose-binding protein, a secreted protein which has been described as a competent fusion partner (Maina et al., Gene 4:365 [1988]) has been used with success. We anticipate that other fusion strategies may also serve to allow proper folding and provide a means to produce authentic, active enterokinase light chain.

C. Expression in *Saccharomyces cerevisiae*

1. PACE

The expression construct described for use in CHO cells utilizing the PACE pre/pro sequence fused to the 5' end of the coding sequence for mature bovine enterokinase catalytic chain can also be used for enterokinase secretion from *Saccharomyces cerevisiae*. This yeast has been shown to produce an enzyme called Kex2 [Julius et. al., Cell 37:1075 (1984)] which cleaves on the C-terminal side of dibasic residues, similarly to PACE. Co-expression of the yeast kex2 gene with the PACE pre/pro-bovine enterokinase light chain construct in COS cells results in complete processing of the PACE pre/pro sequence to yield a product which is immunoprecipitable with bovine enterokinase antisera and co-migrates with PACE-processed enterokinase light chain after separation of the products on SDS-PAGE. Thus, yeast Kex2 recognized and cleaved the PACE cleavage site in the PACE pro-sequence to produce mature enterokinase.

The coding sequence for this chimeric construct (mammalian PACE secretory leader and propeptide sequence followed by the mature bovine enterokinase light chain sequence) was inserted into a yeast expression vector to produce and secrete the fusion protein. The host Kex2 protein is expected to cleave off the PACE pro-peptide following the Arg—Thr—Lys—Arg sequence, resulting in secretion of properly processed mature enterokinase light chain. The Kex2 protein may be co-expressed to increase processing activity if needed. Such over-expression of Kex2 may be accomplished with either the native protein or with a soluble derivative lacking the C-terminal transmembrane domain as described by Brenner et. al., supra. This form of Kex2 is analogous to the soluble PACE co-expressed with the PACE pre/pro-bovine enterokinase light chain used in the CHO cell expression. Alternatively, mammalian PACE can be co-expressed in yeast to accentuate pro-peptide processing of the chimeric enterokinase construct either in the presence or absence of host endogenous levels of Kex2.

2. α-Factor

Alternatively, the coding sequence for mature bovine enterokinase light chain can be fused to the coding sequence for the secretory leader and pro-peptide of, for instance, the α-factor protein from *S. cerevisiae*, a protein which is normally secreted and subsequently processed by Kex2 [Julius et. al., Cell 32:839 (1983)]. This construct is expected to produce material similar to the other construct described above; that is, properly processed and active enterokinase light chain which accumulates in the culture media in active form.

EXAMPLE 9

Co-Expression of Fusion Proteins and Active Enterokinase

A configuration advantageous in some situations co-expresses active enterokinase along with a fusion protein which is to be subsequently cleaved. The fusion can be segregated by cell compartmentalization during cell growth and fusion protein synthesis, thereby allowing the desirable effects of fusion proteins (e.g., stabilization, solubility) to remain. Then, upon cell lysis, the active enterokinase is allowed to mix (co-mingle) with the expressed fusion protein and cleave it, thereby simplifying the downstream processing of the fusion protein. One method for accomplishing this is to secrete active enterokinase into the periplasmic space of *E. coli*, while producing a fusion protein in the cytoplasm. Other methods can be equally suitable, for instance co-secretion of enterokinase and a fusion protein in CHO cells, analogous to the co-secretion of PACE and the PACE pro/enterokinase fusion employed for CHO production of active enterokinase as described, supra. Another method is co-expression of an enterokinase fusion protein (e.g., Trx/enterokinase light chain with an enterokinase cleavage site between them) and a fusion protein containing a desired protein product, also with an enterokinase site between the domains. The enterokinase is expected to remain inactive until purified and until concentrated to the point where autocatalysis occurs, whereupon the co-purified desired fusion protein will also be processed.

EXAMPLE 10

Use of Enterokinase as a Therapeutic Agent

A condition exists in humans whereby the ability to digest protein is severely impaired [Hadorn et al., Lancet 1:812–813(1969); Tarlow et al., Arch. Dis. Child. 45:651–655(1970)]. Studies on these patient have revealed that they are deficient in the production of enterokinase (enteropeptidase), which is necessary for the conversion of trypsinogen to trypsin which in turn activates the numerous pancreatic zymogens responsible for digestion to occur. Duodenal juice from these patients cannot activate trypsinogen in vitro, but addition of purified enterokinase to this duodenal juice results in activation of proteolytic enzymes, suggesting that the inactive zymogens are present and able to be activated [Hadorn et al., supra.]. This condition has been treated in the past with pancreatic extracts.

A recombinant enterokinase may be used as a therapy for this condition. When formulated to allow oral administration, the enzyme enters the duodenum where it encounters the inactive pancreatic zymogens entering from the pancreatic duct. There it activates trypsinogen which in turn activates the other zymogens, and proper digestion proceeds. The human form of enterokinase gene may also be useful in gene therapy to correct this condition.

The foregoing illustrative examples relate to the isolation and characterization of nucleic acid sequences encoding enterokinase activity, as well as the corresponding transcription and translation thereof to yield the corresponding proteins and polypeptides. Also described are the uses of these proteins either as a heavy and light chain together, or a light chain alone.

While the present invention has been described in terms of specific methods and compositions, it is understood that variations and modifications will occur to those skilled in the art upon consideration of the present invention.

Numerous modifications and variations in the invention as described in the above illustrative examples are expected to occur to those skilled in the art and consequently only such limitations as appear in the appended claims be placed thereon. Accordingly, it is intended in the appended claims to cover all such equivalent variations which come within the scope of the invention as claimed.

What is claimed is:

1. An isolated DNA consisting of the nucleic acid sequence of SEQ ID NO: 1 operably linked to a second DNA encoding a region selected from the group consisting of a pre-region, pro-region, and a pre/pro region.

2. The isolated DNA of claim 1, wherein said second DNA is a pre-pro region selected from the group consisting of the pre/pro region of PACE, the pre/pro region of trypsinogen, and the pre/pro region of yeast α-factor.

3. A method for the production of a polypeptide having enterokinase activity comprising:
   (a) disposing the isolated DNA operably linked to the second DNA according to claim 1 in a cell free transcription and translation system, and
   (b) isolating from said system the polypeptide encoded by the isolated DNA operably linked to the second DNA according to claim 1.

4. An isolated DNA encoding enterokinase and corresponding to plasmid pEK-2/GI734, designated as ATCC Deposit No. 69232.

5. An isolated DNA consisting of the nucleic acid sequence of SEQ ID NO: 1.

6. A nucleic acid vector comprising the DNA according to claim 5.

7. A host cell transformed or transfected with the nucleic acid vector of claim 6.

8. A method for producing a polypeptide having enterokinase activity comprising:
   (a) growing, in culture, cell of claim 7, and
   (b) isolating from said host cell or said culture the polypeptide encoded by said DNA.

9. An isolated DNA consisting of a nucleic acid which encodes the amino acid sequence of SEQ ID NO: 2.

10. A nucleic acid vector comprising the DNA according to claim 9.

11. A host cell transformed or transfected with the nucleic acid vector of claim 10.

12. A method for producing a polypeptide having enterokinase activity comprising:
   (a) growing, in culture, of claim 11, and
   (b) isolating from said host cell or said culture the polypeptide encoded by said DNA.

13. An isolated DNA comprising nucleotide 1691 to nucleotide 2398 of SEQ ID No. 1, said DNA encoding a polypeptide having enterokinase activity.

14. The DNA of claim 13 further comprising a second DNA encoding a member selected from the group consisting of a pre-region, pro-region, and a pre/pro region.

15. The DNA of claim 14, wherein said second DNA is a pre/pro region selected from the group consisting of the pre/pro region of PACE, the pre/pro region of trypsinogen, and the pre/pro region of yeast α-factor.

16. The DNA of claim 13, further comprising a second DNA operably linked and encoding thioredoxin.

17. A nucleic acid vector comprising the DNA according to claim 13.

18. The vector of claim 17 further comprising an expression control sequence operatively associated with said DNA.

19. A host cell transformed or transfected with the nucleic acid vector of claim 17.

20. A method for producing a polypeptide having enterokinase activity comprising:

(a) growing, in culture, cell of claim 19, and (b) isolating from said host cell or said culture the polypeptide encoded by said DNA.

* * * * *

UNITED STATES PATENT AND TRADEMARK OFFICE
CERTIFICATE OF CORRECTION

PATENT : 5,665,566
DATED : September 9, 1997
INVENTOR(S) : Edward R. LaVallie

It is certified that error appears in the above-identified patent and that said Letters Patent is hereby corrected as shown below:

In claim 2, please change "pre-pro" to --pre/pro--.
In claim 8, and 20, please change "cell" to the host cell--.
In claim 12, please change "of claim" to --the host cell of claim--.

Signed and Sealed this

First Day of May, 2001

Attest:

NICHOLAS P. GODICI

*Attesting Officer*    *Acting Director of the United States Patent and Trademark Office*

SEQUENCE LISTING ( 1 ) GENERAL INFORMATION:

( i i i ) NUMBER OF SEQUENCES: 38

( 2 ) INFORMATION FOR SEQ ID NO: 1:

( i ) SEQUENCE CHARACTERISTICS:
    ( A ) LENGTH: 2581 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 1:

| | | | | | | |
|---|---|---|---|---|---|---|
| CGGAGCTTGT | GATGGAAGAT | TTTGTTGAC | TGGATCTTCT | GGGTCCTTTG | AGGCTCTGCA | 60 |
| TTATCCCAAG | CCTTCTAATA | ATACAAGCGC | TGTTTGTCGG | TGGATTATAC | GTGTAAACCA | 120 |
| AGGACTTTCC | ATTCAACTGA | ACTTCGATTA | TTTTAATACA | TATTATGCAG | ATGTATTAAA | 180 |
| TATTTATGAA | GGAATGGGTT | CAAGCAAGAT | TTAAGAGCT | TCTCTCTGGT | CAAATAATCC | 240 |
| TGGCATAATT | AGGATTTTTT | CCAATCAAGT | TACTGCCACT | TTCTTATAC | AGTCTGATGA | 300 |
| AAGTGATTAT | ATTGGCTTCA | AAGTAACATA | CACTGCATTT | AACAGCAAAG | AGCTTAATAA | 360 |
| TTATGAGAAA | ATCAACTGTA | ATTTGAAGA | TGGCTTCTGT | TTCTGGATCC | AGGATCTAAA | 420 |
| TGATGACAAT | GAGTGGGAAA | GGACTCAGGG | AAGCACCTTT | CCTCCATCTA | CTGGACCAAC | 480 |
| TTTGACCAC | ACTTTTGGCA | ATGAGTCAGG | ATTTTACATT | TCCACCCCAA | CTGGACCAGG | 540 |
| AGGAAGACGA | GAAAGAGTAG | GACTTTTAAC | TCTCCCTTTA | GATCCACTC | CTGAACAAGC | 600 |
| CTGCCTTAGT | TTCTGGTATT | ATATGTATGG | TGAAAATGTT | TACAAACTAA | GCATTAATAT | 660 |
| CAGCAGTGAC | CAAAACATGG | AGAAGACAAT | TTTCCAAAAA | GAAGGAAATT | ATGGACAAAA | 720 |
| TTGGAACTAT | GGACAAGTAA | CATTAAATGA | AACAGTGGAA | TTTAAGGTTT | CTTTCTATGG | 780 |
| GTTTAAAAAC | CAGATCCTGA | GTGATATAGC | ATTGGATGAC | ATTAGCCTAA | CATATGGGAT | 840 |
| TTGTAATATG | AGTGTCTATC | CAGAACCAAC | TTTAGTCCCA | ACTCCTCCAC | CAGAACTTCC | 900 |
| CACGGACTGT | GGAGGGCCTC | ATGACCTGTG | GGAGCCAAAT | ACAACATTCA | CGTCTATAAA | 960 |
| CTTCCCAAAC | AGCTACCCTA | ATCAGGCTTT | CTGTATTTGG | AATTTAAATG | CACAAAAGGG | 1020 |
| AAAAAATATT | CAGCTCCACT | TTCAAGAATT | TGACCTGGAA | AATATTGCAG | ATGTAGTTGA | 1080 |
| AATCAGAGAT | GGTGAAGGAG | ATGATTCCTT | GTTCTTAGCT | GTGTACACAG | GCCCTGGTCC | 1140 |
| AGTAAACGAT | GTGTTCTCAA | CCACCAACCG | AATGACTGTG | CTTTTATCA | CTGATAATAT | 1200 |
| GCTGGCAAAA | CAGGGATTTA | AAGCAAATTT | CACTACTGGC | TATGGCTTGG | GGATTCCAGA | 1260 |
| ACCCTGCAAG | GAAGACAATT | TCAGTGCAA | GGATGGGGAG | TGTATTCCGC | TGGTGAATCT | 1320 |
| CTGTGACGGT | TTTCCACACT | GTAAGGATGG | CTCAGATGAA | GCACACTGTG | TGCGTCTCTT | 1380 |
| CAATGGCACG | ACAGACAGCA | GTGGTTTGGT | GCAGTTCAGG | ATCCAAAGCA | TATGGCATGT | 1440 |
| AGCCTGTGCC | GAGAACTGGA | CAACCCAGAT | CTCAGATGAT | GTGTGTCAGC | TGCTGGGACT | 1500 |
| AGGGACTGGA | AACTCATCCG | TGCCAACCTT | TTCTACTGGA | GGTGGACCAT | ATGTAAATTT | 1560 |
| AAACACAGCA | CCTAATGGCA | GCTTAATACT | AACGCCAAGC | CAACAGTGCT | TAGAGGATTC | 1620 |
| ACTGATTTTG | CTACAATGTA | ACTACAAATC | ATGTGGGAAA | AAACTGGTGA | CTCAAGAAGT | 1680 |
| TAGCCCGAAG | ATTGTCGGAG | GAAGTGACTC | CAGAGAAGGA | GCCTGGCCTT | GGGTCGTTGC | 1740 |
| TCTGTATTTC | GACGATCAAC | AGGTCTGCGG | AGCTTCTCTG | GTGAGCAGGG | ATTGGCTGGT | 1800 |
| GTCGGCCGCC | CACTGCGTGT | ACGGGAGAAA | TATGGAGCCG | TCTAAGTGGA | AAGCAGTGCT | 1860 |
| AGGCCTGCAT | ATGGCATCAA | ATCTGACTTC | TCCTCAGATA | GAAACTAGGT | TGATTGACCA | 1920 |
| AATTGTCATA | AACCCACACT | ACAATAAACG | GAGAAGAAC | AATGACATTG | CCATGATGCA | 1980 |
| TCTTGAAATG | AAAGTGAACT | ACACAGATTA | TATACAGCCT | ATTTGTTTAC | AGAAGAAAA | 2040 |
| TCAAGTTTTT | CCCCCAGGAA | GAATTTGTTC | TATTGCTGGC | TGGGGGGCAC | TTATATATCA | 2100 |

```
AGGTTCTACT GCAGACGTAC TGCAAGAAGC TGACGTTCCC CTTCTATCAA ATGAGAAATG    2160

TCAACAACAG ATGCCAGAAT ATAACATTAC GGAAAATATG GTGTGTGCAG GCTATGAAGC    2220

AGGAGGGGTA GATTCTTGTC AGGGGGATTC AGGCGGACCA CTCATGTGCC AAGAAAACAA    2280

CAGATGGCTC CTGGCTGGCG TGACGTCATT TGGATATCAA TGTGCACTGC CTAATCGCCC    2340

AGGGGTGTAT GCCCGGGTCC CAAGGTTCAC AGAGTGGATA CAAAGTTTTC TACATTAGAG    2400

TGTTTCCAGA AACAAAGATG AAAATCAGGC AGTTTTCCCA TTTCACTTTA AGAAGCATGG    2460

AAATTGAGAG TTAAAAAAAT AATAATTTAT AAAAGTCTTG ATTCTTACCT AAGGCACTGA    2520

AATGCTACAA AAAAAAAAAA ACCGGAATTC AGCTTGGACT TAACCAGGCT GAACTTGCGG    2580

C                                                                    2581
```

( 2 ) INFORMATION FOR SEQ ID NO: 2:

( i ) SEQUENCE CHARACTERISTICS:
        ( A ) LENGTH: 798 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 2:

```
Gly Ala Cys Asp Gly Arg Phe Leu Leu Thr Gly Ser Ser Gly Ser Phe
 1           5                  10                  15

Glu Ala Leu His Tyr Pro Lys Pro Ser Asn Asn Thr Ser Ala Val Cys
            20                  25                  30

Arg Trp Ile Ile Arg Val Asn Gln Gly Leu Ser Ile Gln Leu Asn Phe
        35                  40                  45

Asp Tyr Phe Asn Thr Tyr Tyr Ala Asp Val Leu Asn Ile Tyr Glu Gly
    50                  55                  60

Met Gly Ser Ser Lys Ile Leu Arg Ala Ser Leu Trp Ser Asn Asn Pro
65                  70                  75                  80

Gly Ile Ile Arg Ile Phe Ser Asn Gln Val Thr Ala Thr Phe Leu Ile
                85                  90                  95

Gln Ser Asp Glu Ser Asp Tyr Ile Gly Phe Lys Val Thr Tyr Thr Ala
            100                 105                 110

Phe Asn Ser Lys Glu Leu Asn Asn Tyr Glu Lys Ile Asn Cys Asn Phe
        115                 120                 125

Glu Asp Gly Phe Cys Phe Trp Ile Gln Asp Leu Asn Asp Asp Asn Glu
    130                 135                 140

Trp Glu Arg Thr Gln Gly Ser Thr Phe Pro Pro Ser Thr Gly Pro Thr
145                 150                 155                 160

Phe Asp His Thr Phe Gly Asn Glu Ser Gly Phe Tyr Ile Ser Thr Pro
                165                 170                 175

Thr Gly Pro Gly Gly Arg Arg Glu Arg Val Gly Leu Leu Thr Leu Pro
            180                 185                 190

Leu Asp Pro Thr Pro Glu Gln Ala Cys Leu Ser Phe Trp Tyr Tyr Met
        195                 200                 205

Tyr Gly Glu Asn Val Tyr Lys Leu Ser Ile Asn Ile Ser Ser Asp Gln
    210                 215                 220

Asn Met Glu Lys Thr Ile Phe Gln Lys Glu Gly Asn Tyr Gly Gln Asn
225                 230                 235                 240

Trp Asn Tyr Gly Gln Val Thr Leu Asn Glu Thr Val Glu Phe Lys Val
                245                 250                 255
```

```
Ser Phe Tyr Gly Phe Lys Asn Gln Ile Leu Ser Asp Ile Ala Leu Asp
            260             265             270

Asp Ile Ser Leu Thr Tyr Gly Ile Cys Asn Met Ser Val Tyr Pro Glu
        275             280             285

Pro Thr Leu Val Pro Thr Pro Pro Glu Leu Pro Thr Asp Cys Gly
    290             295             300

Gly Pro His Asp Leu Trp Glu Pro Asn Thr Thr Phe Thr Ser Ile Asn
305             310             315                 320

Phe Pro Asn Ser Tyr Pro Asn Gln Ala Phe Cys Ile Trp Asn Leu Asn
                325             330             335

Ala Gln Lys Gly Lys Asn Ile Gln Leu His Phe Gln Glu Phe Asp Leu
            340             345             350

Glu Asn Ile Ala Asp Val Val Glu Ile Arg Asp Gly Glu Gly Asp Asp
            355             360             365

Ser Leu Phe Leu Ala Val Tyr Thr Gly Pro Gly Pro Val Asn Asp Val
    370             375             380

Phe Ser Thr Thr Asn Arg Met Thr Val Leu Phe Ile Thr Asp Asn Met
385             390             395                 400

Leu Ala Lys Gln Gly Phe Lys Ala Asn Phe Thr Thr Gly Tyr Gly Leu
            405             410             415

Gly Ile Pro Glu Pro Cys Lys Glu Asp Asn Phe Gln Cys Lys Asp Gly
            420             425             430

Glu Cys Ile Pro Leu Val Asn Leu Cys Asp Gly Phe Pro His Cys Lys
        435             440             445

Asp Gly Ser Asp Glu Ala His Cys Val Arg Leu Phe Asn Gly Thr Thr
    450             455             460

Asp Ser Ser Gly Leu Val Gln Phe Arg Ile Gln Ser Ile Trp His Val
465             470             475                 480

Ala Cys Ala Glu Asn Trp Thr Thr Gln Ile Ser Asp Asp Val Cys Gln
            485             490             495

Leu Leu Gly Leu Gly Thr Gly Asn Ser Ser Val Pro Thr Phe Ser Thr
        500             505             510

Gly Gly Gly Pro Tyr Val Asn Leu Asn Thr Ala Pro Asn Gly Ser Leu
        515             520             525

Ile Leu Thr Pro Ser Gln Gln Cys Leu Glu Asp Ser Leu Ile Leu Leu
    530             535             540

Gln Cys Asn Tyr Lys Ser Cys Gly Lys Lys Leu Val Thr Gln Glu Val
545             550             555                 560

Ser Pro Lys Ile Val Gly Gly Ser Asp Ser Arg Glu Gly Ala Trp Pro
            565             570             575

Trp Val Val Ala Leu Tyr Phe Asp Asp Gln Gln Val Cys Gly Ala Ser
            580             585             590

Leu Val Ser Arg Asp Trp Leu Val Ser Ala Ala His Cys Val Tyr Gly
        595             600             605

Arg Asn Met Glu Pro Ser Lys Trp Lys Ala Val Leu Gly Leu His Met
    610             615             620

Ala Ser Asn Leu Thr Ser Pro Gln Ile Glu Thr Arg Leu Ile Asp Gln
625             630             635                 640

Ile Val Ile Asn Pro His Tyr Asn Lys Arg Arg Lys Asn Asn Asp Ile
            645             650             655

Ala Met Met His Leu Glu Met Lys Val Asn Tyr Thr Asp Tyr Ile Gln
            660             665             670

Pro Ile Cys Leu Pro Glu Glu Asn Gln Val Phe Pro Pro Gly Arg Ile
        675             680             685
```

```
Cys  Ser  Ile  Ala  Gly  Trp  Gly  Ala  Leu  Ile  Tyr  Gln  Gly  Ser  Thr  Ala
     690                 695                 700
Asp  Val  Leu  Gln  Glu  Ala  Asp  Val  Pro  Leu  Leu  Ser  Asn  Glu  Lys  Cys
705                      710                 715                           720
Gln  Gln  Gln  Met  Pro  Glu  Tyr  Asn  Ile  Thr  Glu  Asn  Met  Val  Cys  Ala
               725                      730                      735
Gly  Tyr  Glu  Ala  Gly  Gly  Val  Asp  Ser  Cys  Gln  Gly  Asp  Ser  Gly  Gly
               740                 745                           750
Pro  Leu  Met  Cys  Gln  Glu  Asn  Asn  Arg  Trp  Leu  Leu  Ala  Gly  Val  Thr
               755                 760                      765
Ser  Phe  Gly  Tyr  Gln  Cys  Ala  Leu  Pro  Asn  Arg  Pro  Gly  Val  Tyr  Ala
     770                      775                      780
Arg  Val  Pro  Arg  Phe  Thr  Glu  Trp  Ile  Gln  Ser  Phe  Leu  His
785                      790                 795
```

( 2 ) INFORMATION FOR SEQ ID NO: 3:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 3:

```
Ile  Val  Gly  Gly  Ser  Asp  Ser  Tyr  Glu  Gly  Ala  Trp  Pro  Trp  Val  Val
1                   5                   10                            15
Ala  Leu  Tyr  Phe  Asp  Asp  Gln  Gln  Val  Cys  Gly
               20                  25
```

( 2 ) INFORMATION FOR SEQ ID NO: 4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 4:

CTCGAATTCA TGTGGGGTCG A                                           21

( 2 ) INFORMATION FOR SEQ ID NO: 5:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 5:

CTCGAATTCA TGTGGGGAGG A                                           21

( 2 ) INFORMATION FOR SEQ ID NO: 6:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear (  i i  ) MOLECULE TYPE: protein ( x i ) SEQUENCE DESCRIPTION: SEQ ID NO: 6:

Asp Gln Gln Val Cys Gly
1               5

( 2 ) INFORMATION FOR SEQ ID NO: 7:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 7:

TCCAAGCTTC CCAACTGTGT C                                                            2 1

( 2 ) INFORMATION FOR SEQ ID NO: 8:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO: 8:

Tyr Glu Gly Ala Trp Pro
1               5

( 2 ) INFORMATION FOR SEQ ID NO: 9:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 9:

TAY GARGGNG CNTGGCC                                                                1 7

( 2 ) INFORMATION FOR SEQ ID NO: 10:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: protein ( x i ) SEQUENCE DESCRIPTION: SEQ ID NO: 10:

Phe Asp Asp Gln Gln Val
1               5

( 2 ) INFORMATION FOR SEQ ID NO: 11:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO: 11:

TCCAAGCTTA CTGTGTCTCA A 21

( 2 ) INFORMATION FOR SEQ ID NO: 12:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 12:

```
Ile Val Gly Gly Ser Asp Ser Arg Glu Gly Ala Trp Pro Trp Val Val
 1               5                  10                  15
Ala Leu Tyr Phe Asp Asp Gln Gln Val Cys Gly Ala Ser Leu
             20                  25                  30
```

( 2 ) INFORMATION FOR SEQ ID NO: 13:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 13:

```
Glu Gly Ala Trp Pro Trp Val Val Ala Leu Tyr Phe Asp Asp Gln Gln
 1               5                  10                  15
Val Cys Gly Ala Ser Leu Val Ser
             20
```

( 2 ) INFORMATION FOR SEQ ID NO: 14:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 14:

```
Asp Trp Leu Val Ser Ala Ala His Cys Val Tyr Gly Arg
 1               5                  10
```

( 2 ) INFORMATION FOR SEQ ID NO: 15:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 15:

```
Phe Thr Glu Trp Ile Gln Ser Phe Leu His
 1               5                  10
```

( 2 ) INFORMATION FOR SEQ ID NO: 16:

( i ) SEQUENCE CHARACTERISTICS:
        ( A ) LENGTH: 23 amino acids
        ( B ) TYPE: amino acid (C) STRANDEDNESS: single
(D) TOPOLOGY: linear (ii) MOLECULE TYPE: protein (xi) SEQUENCE DESCRIPTION: SEQ ID NO: 16:

```
Ile Cys Ser Ile Ala Gly Trp Gly Ala Leu Ile Tyr Gln Gly Ser Thr
1               5                   10                  15
Ala Asp Val Leu Gln Glu Ala
                20
```

(2) INFORMATION FOR SEQ ID NO: 17:

(i) SEQUENCE CHARACTERISTICS:
    (A) LENGTH: 23 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 17:

```
Trp Leu Leu Ala Gly Val Thr Ser Phe Gly Tyr Gln Cys Ala Leu Pro
1               5                   10                  15
Asn Asn Pro Gly Val Tyr Ala
                20
```

(2) INFORMATION FOR SEQ ID NO: 18:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: protein (xi) SEQUENCE DESCRIPTION: SEQ ID NO: 18:

```
Asn Met Glu Pro Ser Lys
1               5
```

(2) INFORMATION FOR SEQ ID NO: 19:

(i) SEQUENCE CHARACTERISTICS:
    (A) LENGTH: 26 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 19:

CGCGGATCCC CRTANACRCA RTGNGC    26

(2) INFORMATION FOR SEQ ID NO: 20:

(i) SEQUENCE CHARACTERISTICS:
    (A) LENGTH: 28 base pairs
    (B) TYPE: nucleic acid
    (C) STRANDEDNESS: single
    (D) TOPOLOGY: linear (ii) MOLECULE TYPE: cDNA (xi) SEQUENCE DESCRIPTION: SEQ ID NO: 20:

CCGGAATTCT TGGGTCGTTG CTCTGTAT    28

(2) INFORMATION FOR SEQ ID NO: 21:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO: 21:

CGCGGATCCA TACAGAGCAA CGACCCAA    28

( 2 ) INFORMATION FOR SEQ ID NO: 22:

( i ) SEQUENCE CHARACTERISTICS:
  ( A ) LENGTH: 9 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO: 22:

Leu Val Thr Gln Glu Val Ser Pro Lys
1               5

( 2 ) INFORMATION FOR SEQ ID NO: 23:

( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO: 23:

Ala Phe Thr Thr Gly Tyr Gly Leu Gly Ile Pro Glu Pro
1               5                   10

( 2 ) INFORMATION FOR SEQ ID NO: 24:

( i ) SEQUENCE CHARACTERISTICS:
  ( A ) LENGTH: 13 amino acids
  ( B ) TYPE: amino acid
  ( C ) STRANDEDNESS: single
  ( D ) TOPOLOGY: linear ( i i ) MOLECULE TYPE: protein ( x i ) SEQUENCE DESCRIPTION: SEQ ID NO: 24:

Leu Phe Gly Thr Thr Asp Ser Ser Gly Leu Val Gln Phe
1               5                   10

( 2 ) INFORMATION FOR SEQ ID NO: 25:

( i ) SEQUENCE CHARACTERISTICS:
  ( A ) LENGTH: 23 base pairs
  ( B ) TYPE: nucleic acid
  ( C ) STRANDEDNESS: single
  ( D ) TOPOLOGY: linear ( i i ) MOLECULE TYPE: cDNA ( x i ) SEQUENCE DESCRIPTION: SEQ ID NO: 25:

CTATAGACTG CTGGGTAGTC CCC    23

( 2 ) INFORMATION FOR SEQ ID NO: 26:

( i ) SEQUENCE CHARACTERISTICS:

( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 26:

ATAAGAATGC GGCCGCAAGT TCAGCCTGGT TAAGTCCAAG C  41

( 2 ) INFORMATION FOR SEQ ID NO: 27:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 27:

CCAAATACAG AAAGCCTGAT TAGGG  25

( 2 ) INFORMATION FOR SEQ ID NO: 28:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO: 28:

GTAGGTCGAC CGTGAATGTT GTATTGGCT CCC  33

( 2 ) INFORMATION FOR SEQ ID NO: 29:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 29:

Leu Ser Ile Asn Ile Ser Ser Asp Gln Asn Met Glu Lys
    1               5                   10

( 2 ) INFORMATION FOR SEQ ID NO: 30:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 30:

Val Ser Phe Tyr Gly Phe Lys
    1               5

( 2 ) INFORMATION FOR SEQ ID NO: 31:

( i ) SEQUENCE CHARACTERISTICS:
        ( A ) LENGTH: 20 amino acids
        ( B ) TYPE: amino acid
        ( C ) STRANDEDNESS: single (D) TOPOLOGY: linear (i i) MOLECULE TYPE: protein (x i) SEQUENCE DESCRIPTION: SEQ ID NO: 31:

```
Gln Lys Glu Gly Asn Tyr Gly Gln Asn Trp Asn Tyr Gly Gln Val Thr
1               5                   10                  15
Leu Asn Glu Thr
            20
```

(2) INFORMATION FOR SEQ ID NO: 32:

(i) SEQUENCE CHARACTERISTICS:
    (A) LENGTH: 7 amino acids
    (B) TYPE: amino acid
    (C) STRANDEDNESS: single
    (D) TOPOLOGY: linear (i i) MOLECULE TYPE: protein (x i) SEQUENCE DESCRIPTION: SEQ ID NO: 32:

```
Val Gly Leu Leu Thr Leu Pro
1               5
```

(2) INFORMATION FOR SEQ ID NO: 33:

(i) SEQUENCE CHARACTERISTICS:
    (A) LENGTH: 5 amino acids
    (B) TYPE: amino acid
    (C) STRANDEDNESS: single
    (D) TOPOLOGY: linear (i i) MOLECULE TYPE: protein (x i) SEQUENCE DESCRIPTION: SEQ ID NO: 33:

```
Thr Ile Phe Gln Lys
1               5
```

(2) INFORMATION FOR SEQ ID NO: 34:

(i) SEQUENCE CHARACTERISTICS:
    (A) LENGTH: 5 amino acids
    (B) TYPE: amino acid
    (C) STRANDEDNESS: single
    (D) TOPOLOGY: linear (i i) MOLECULE TYPE: protein (x i) SEQUENCE DESCRIPTION: SEQ ID NO: 34:

```
Asp Asp Asp Asp Lys
1               5
```

(2) INFORMATION FOR SEQ ID NO: 35:

(i) SEQUENCE CHARACTERISTICS:
    (A) LENGTH: 6 amino acids
    (B) TYPE: amino acid
    (C) STRANDEDNESS: single
    (D) TOPOLOGY: linear (i i) MOLECULE TYPE: protein (x i) SEQUENCE DESCRIPTION: SEQ ID NO: 35:

```
Gly Asp Asp Asp Asp Lys
1               5
```

(2) INFORMATION FOR SEQ ID NO: 36:

(i) SEQUENCE CHARACTERISTICS:

```
        ( A ) LENGTH: 4 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO: 36:

Arg  Thr  Lys  Arg
     1

( 2 ) INFORMATION FOR SEQ ID NO: 37:

( i ) SEQUENCE CHARACTERISTICS:
            ( A ) LENGTH: 11 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO: 37:

Gly  Ser  Gly  Ser  Gly  Asp  Asp  Asp  Asp  Lys  Asn
     1                   5                        10

( 2 ) INFORMATION FOR SEQ ID NO: 38:

( i ) SEQUENCE CHARACTERISTICS:
            ( A ) LENGTH: 4 amino acids
            ( B ) TYPE: amino acid
            ( C ) STRANDEDNESS: single
            ( D ) TOPOLOGY: linear ( i i ) MOLECULE TYPE: protein ( x i ) SEQUENCE DESCRIPTION: SEQ ID NO: 38:

Arg  Thr  Lys  Arg
     1
```